US008728080B2

(12) United States Patent
Boomer et al.

(10) Patent No.: US 8,728,080 B2
(45) Date of Patent: May 20, 2014

(54) SPINAL FIXATION PLATES AND PLATE EXTENSIONS

(75) Inventors: Mark C. Boomer, Irvine, CA (US); Iain Kalfas, Beachwood, OH (US); Raymond F. Murphy, Attleboro, MA (US)

(73) Assignee: DePuy Spine SARL, LeLocle (CH)

( * ) Notice: Subject to any disclaimer, the term of this patent is extended or adjusted under 35 U.S.C. 154(b) by 771 days.

(21) Appl. No.: 12/499,287

(22) Filed: Jul. 8, 2009

(65) Prior Publication Data

US 2010/0010541 A1 Jan. 14, 2010

Related U.S. Application Data

(62) Division of application No. 10/830,621, filed on Apr. 23, 2004, now Pat. No. 7,572,282.

(51) Int. Cl.
*A61B 17/56* (2006.01)
*A61B 17/70* (2006.01)
*A61B 17/80* (2006.01)

(52) U.S. Cl.
USPC .............. 606/71; 606/280; 606/902; 606/903

(58) Field of Classification Search
USPC ............. 606/70, 71, 280, 282, 295, 296, 902, 606/903
See application file for complete search history.

(56) References Cited

U.S. PATENT DOCUMENTS

| 2,004,182 A | 6/1935 | Arey |
| 3,654,053 A | 4/1972 | Toedter |
| 4,771,767 A | 9/1988 | Steffee |
| 4,778,321 A | 10/1988 | Okawa |
| 4,865,025 A * | 9/1989 | Buzzi et al. ..................... 606/96 |
| 5,002,542 A | 3/1991 | Frigg |
| 5,084,048 A | 1/1992 | Jacob |
| 5,209,752 A | 5/1993 | Ashman |
| 5,344,422 A | 9/1994 | Frigg |
| 5,360,429 A | 11/1994 | Jeanson et al. |

(Continued)

FOREIGN PATENT DOCUMENTS

| WO | 0106939 A1 | 2/2001 |
| WO | 0215806 A1 | 2/2002 |

OTHER PUBLICATIONS

Brochure: Blackstone Medical Inc., "Bottom to Top, Fixation From T3 to Occiput," Oct. 2003.

(Continued)

*Primary Examiner* — Christian Sevilla
(74) *Attorney, Agent, or Firm* — Nutter McClennen & Fish LLP

(57) ABSTRACT

A spinal fixation plate that is adapted to be implanted in a variety of positions in the occiput is provided. In general, the plate has a substantially planar configuration and it includes a mid-line or central portion having several thru-bores formed therein, and first and second opposed branch portions that extend from the central portion and that also include at least one thru-bore formed therein. The configuration of the branch portions relative to the central portion, as well as the position of the mid-line thru-bores formed in the central portion in relation to the thru-bore(s) formed in each branch portion, allow the spinal fixation plate to be implanted in a variety of positions in the occiput, thus allowing the optimal implant site to be selected.

19 Claims, 10 Drawing Sheets

(56) References Cited

U.S. PATENT DOCUMENTS

| | | | |
|---|---|---|---|
| 5,372,598 A | 12/1994 | Luhr et al. | |
| 5,470,333 A | 11/1995 | Ray | |
| 5,507,745 A | 4/1996 | Logroscino et al. | |
| 5,531,747 A | 7/1996 | Ray | |
| 5,575,791 A | 11/1996 | Lin | |
| 5,582,612 A | 12/1996 | Lin | |
| 5,613,968 A | 3/1997 | Lin | |
| 5,667,506 A | 9/1997 | Sutterlin | |
| 5,725,528 A | 3/1998 | Errico | |
| 5,741,255 A | 4/1998 | Krag et al. | |
| 5,888,221 A | 3/1999 | Gelbard | |
| 5,938,663 A | 8/1999 | Petreto | |
| 5,951,557 A * | 9/1999 | Luter | 606/286 |
| 6,050,997 A | 4/2000 | Mullane | |
| 6,063,089 A | 5/2000 | Errico et al. | |
| 6,106,526 A | 8/2000 | Harms et al. | |
| 6,146,382 A | 11/2000 | Hurlbert | |
| 6,146,384 A | 11/2000 | Lee et al. | |
| 6,197,028 B1 | 3/2001 | Ray et al. | |
| 6,224,602 B1 * | 5/2001 | Hayes | 606/296 |
| 6,299,614 B1 | 10/2001 | Kretschmer | |
| 6,342,055 B1 | 1/2002 | Eisermann et al. | |
| 6,355,038 B1 | 3/2002 | Pisharodi | |
| 6,375,656 B1 | 4/2002 | Faure | |
| 6,413,257 B1 | 7/2002 | Lin et al. | |
| 6,423,064 B1 | 7/2002 | Kluger | |
| 6,485,491 B1 | 11/2002 | Farris et al. | |
| 6,524,315 B1 | 2/2003 | Selvitelli et al. | |
| 6,547,790 B2 | 4/2003 | Harkey, III et al. | |
| 6,602,256 B1 | 8/2003 | Hayes | |
| 6,641,583 B2 | 11/2003 | Shluzas et al. | |
| 7,232,441 B2 | 6/2007 | Altarac et al. | |
| 2002/0188296 A1 * | 12/2002 | Michelson | 606/71 |
| 2003/0036759 A1 * | 2/2003 | Musso | 606/69 |
| 2003/0153913 A1 | 8/2003 | Altarac | |
| 2004/0039385 A1 | 2/2004 | Mazda et al. | |
| 2004/0092947 A1 | 5/2004 | Foley | |
| 2004/0117016 A1 * | 6/2004 | Abramson | 623/16.11 |
| 2004/0153070 A1 | 8/2004 | Barker et al. | |
| 2004/0210220 A1 | 10/2004 | Tornier | |
| 2005/0240185 A1 | 10/2005 | Boomer et al. | |
| 2005/0283152 A1 | 12/2005 | Lindemann et al. | |

OTHER PUBLICATIONS

Brochure: Synthes Spine, "The StarLock Components for Use with the CerviFix System Technique Guide", Oct. 2002.

* cited by examiner

SPINAL FIXATION PLATES AND PLATE EXTENSIONS

CROSS REFERENCE TO RELATED APPLICATIONS

The present application is a divisional of U.S. application Ser. No. 10/830,621 filed on Apr. 23, 2004 and entitled "Spinal Fixation Plates and Plate Extensions," which is hereby incorporated by reference in its entirety

FIELD OF THE INVENTION

The present invention relates to spinal fixation devices, and in particular to a spinal fixation plate that can be used in multiple orientations in a patient's spinal system.

BACKGROUND OF THE INVENTION

Treatment of some spinal injuries or disorders may involve the use of a spinal fixation element, such as a relatively rigid fixation rod, that is coupled to adjacent vertebrae by attaching the element to various anchoring devices, such as plates, hooks, bolts, wires, or screws. Often two rods are disposed on opposite sides of the spinous process in a substantially parallel relationship. The fixation rods can have a predetermined contour that has been designed according to the properties of the target implantation site, and once installed, the rods hold the vertebrae in a desired spatial relationship, until healing or spinal fusion has taken place, or for some longer period of time. When such surgery is performed in the cervical spine, the proximal ends of the rods are typically molded according to the anatomy of the skull and the cervical spine, and attached to a fixation plate that is implanted in the occiput.

There are currently two types of plates that are typically used in the occiput: a T-shaped plate and a Y-shaped plate. The T-shaped plate is designed to maximize the amount of bone graft that can be disposed between the cervical spine and the foremen magnum. When implanted, its shape requires that it be positioned just below the superior nuchal line. As a result, the rod-to-plate connection occurs at a higher location in the occiput, thus becoming more noticeable to the patient. The Y-shaped plate, on the other hand, is configured to sit below and just inside of the inferior nuchal line. Thus, the rod-to-plate attachment occurs at a lower position in the occiput, thereby providing a low-profile connection that is less noticeable to the user. However, because the area between the cervical spine and the occiput is greatly reduced, the use of bone graft material with the Y-shaped plate is limited.

While these plate constructs have provided a stable technique for occipito-cervical fixation, fixation to the occiput continues to be a challenge. In particular, extreme variability in the thickness of the skull itself can limit the effectiveness of current plates, which must be positioned at a particular location in the occiput, even if such a position is not optimal. As a result, the effectiveness of the plate is largely dependent on the positioning of the holes in the plate, as the fixed hole-hole distances in the plate can make proper insertion of the screws difficult. Other complications associated with any internal fixation device, such as hardware loosening, hardware pull out, and hardware fracture, for example, can also occur.

Accordingly, the present invention advantageously provides a spinal fixation plate that can be placed in various locations in the occiput, thus allowing the plate to be implanted at the thickest bone for increased safety as well as optimal stability.

SUMMARY OF THE INVENTION

The present invention provides an implantable spinal fixation plate that is adapted for placement in a variety of locations in the occiput. In an exemplary embodiment, the plate has an elongate central portion with proximal and distal ends that define a longitudinal axis extending therebetween. A first and second thru-bores are formed in the central portion of the plate, and the second thru-bore is preferably positioned distal of the first thru-bore. The plate also includes first and second elongate branch portions that extend from opposed sides of the central portion and that define first and second central axes that are positioned at an angle relative to the longitudinal axis of the central portion. The first and second central axes preferably intersect at an intersection point that is distal to a substantial midpoint of the first thru-bore formed in the central portion, and that is proximal to a substantial midpoint of the second thru-bore formed in the central portion. More preferably, the intersection point is positioned distal to the first thru-bore and proximal to the second thru-bore. The intersection point can also resides along the longitudinal axis of the central portion.

Each branch portion can include at least one thru-bore formed therein, and more preferably each of the first and second branch portions includes a single thru-bore formed therein adjacent to a terminal end thereof. The thru-bore(s) in each of the first and second branch portions can have an oblong shape, or alternatively the thru-bores can have a circular shape. In another embodiment, the thru-bore(s) in each of the first and second branch portions can include a substantially cylindrical member extending therefrom and having threads formed therein.

In another embodiment of the present invention, the central portion and the first and second branch portions extend along a horizontal plane, and the plate includes a bend zone formed between the central portion and each of the first and second branch portions for allowing the first and second branch portions to be positioned at an angle relative to the horizontal plane in which the central portion lies. The bend zone preferably extends along an axis that is substantially parallel to the longitudinal axis of the central portion, and each bend zone can be formed from, for example, at least one channel formed on a surface of the plate. In an exemplary embodiment, each bend zone is in the form of opposed channels formed on opposed surfaces of the plate.

The present invention also provides at least one elongate extension member that is removably matable to the spinal fixation plate and that has a plurality of thru-bores formed therein. In one embodiment, the elongate extension member includes at least two thru-bores, and a clamp member formed thereon for receiving and engaging a spinal fixation element. In another embodiment, the elongate extension member has a central thru-bore formed therein, and first and second thru-bores formed on opposed sides of the central thru-bore. The central thru-bore is adapted to receive a fastening element for removably mating the elongate extension to the first thru-bore in the central portion of the spinal fixation plate. In yet another embodiment, the first and second thru-bores are formed through opposed terminal ends of the elongate extension member, and the opposed terminal ends extend in a plane that is substantially parallel to but spaced apart from a plane defined by a central portion of the extension member that contains the central thru-bore.

The present invention also provides a spinal fixation kit that includes a spinal fixation plate having an elongate central portion with first and second thru-bores formed therein and positioned along a longitudinal axis thereof, and first and second elongate branch portions that extend from opposed sides of the central portion at a location that is substantially between the first and second thru-bores formed in the central portion. Each branch portion includes at least one thru-bore formed therein. The kit also includes at least one extension plate having a plurality of thru-bores formed therein, and the extension plate is removably matable to the spinal fixation plate.

In yet another embodiment of the present invention, a spinal fixation kit is provided and it includes a spinal fixation plate having at least one thru-bore formed therein and a mating element formed thereon, and at least one extension plate having a plurality of thru-bores formed therein and a complementary mating element formed thereon such that the at least one extension plate is slidably matable with the spinal fixation plate. The mating elements can be, for example, dovetail components.

BRIEF DESCRIPTION OF THE DRAWINGS

The invention will be more fully understood from the following detailed description taken in conjunction with the accompanying drawings, in which.

DETAILED DESCRIPTION OF THE INVENTION

The present invention provides a spinal fixation plate that is adapted to be implanted in a variety of positions in the occiput. In general, the plate has a substantially planar configuration and it includes a mid-line or central portion having several thru-bores formed therein, and first and second opposed branch portions that extend from the central portion and that also include at least one thru-bore formed therein. The configuration of the branch portions relative to the central portion, as well as the position of the mid-line thru-bores formed in the central portion in relation to the thru-bore(s) formed in each branch portion, allow the spinal fixation plate to be implanted in a variety of positions in the occiput, thus allowing the optimal implant site to be selected. The configuration also allows a variety of other spinal fixation devices, such as spinal rods, cables, plates, etc. to be attached to the plate in an optimal position.

Figure 1A:
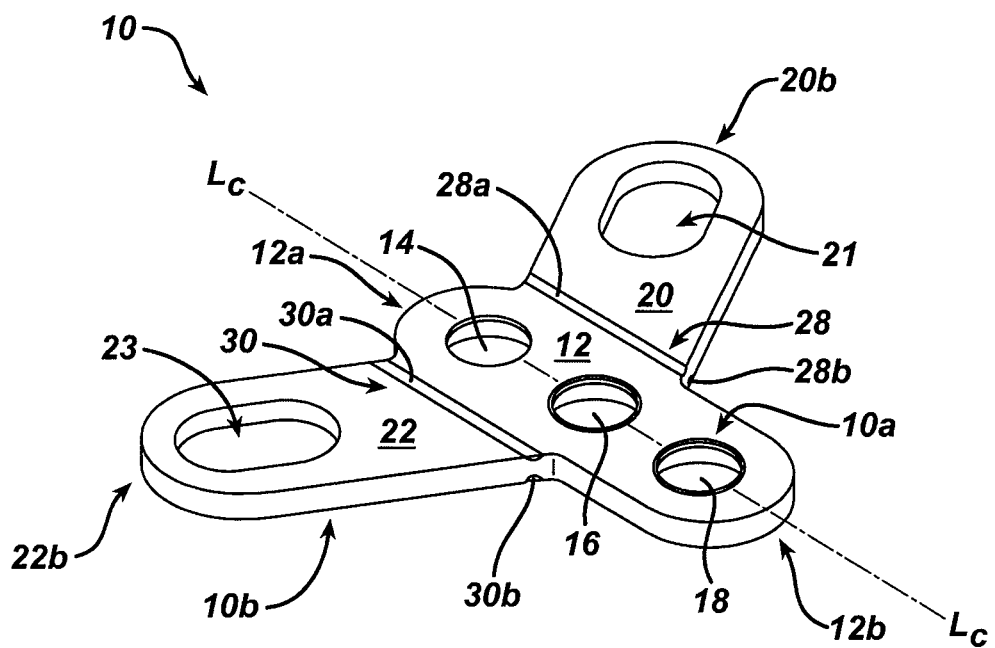
FIG. 1A is a top perspective view of one embodiment of a spinal fixation plate according to the present invention.
Figure 1B:
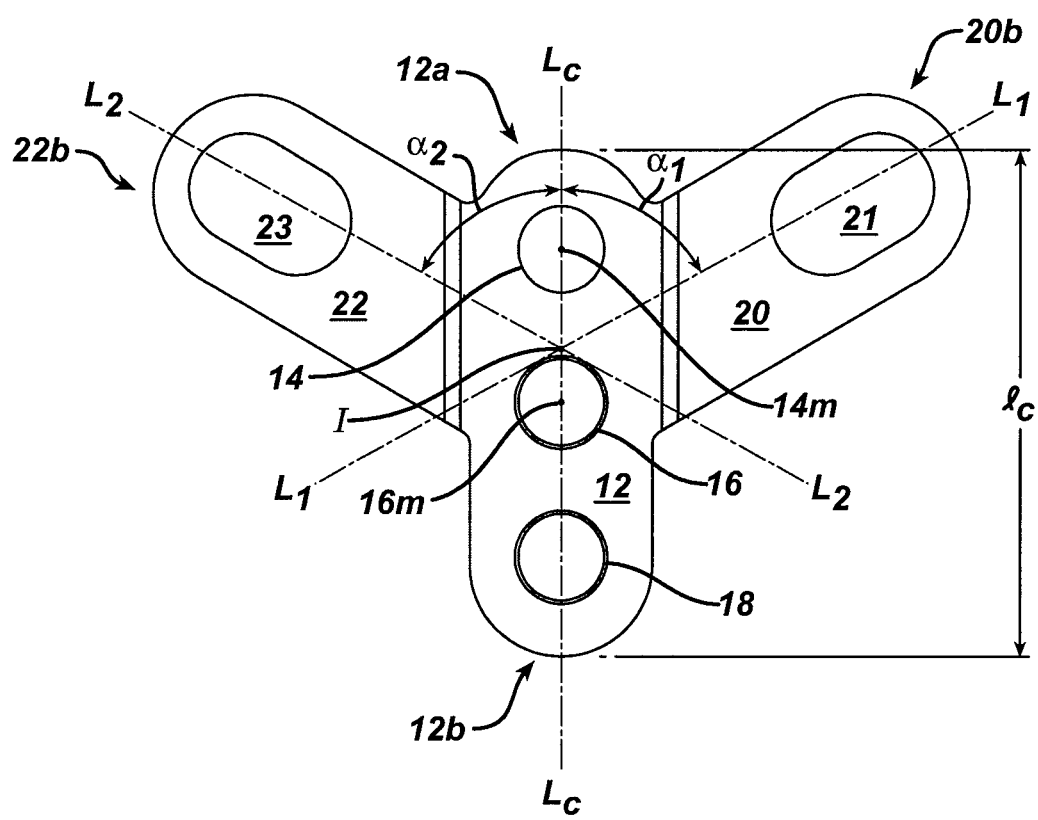
FIG. 1B is a top view of the spinal fixation plate shown in FIG. 1A.
Figure 2:
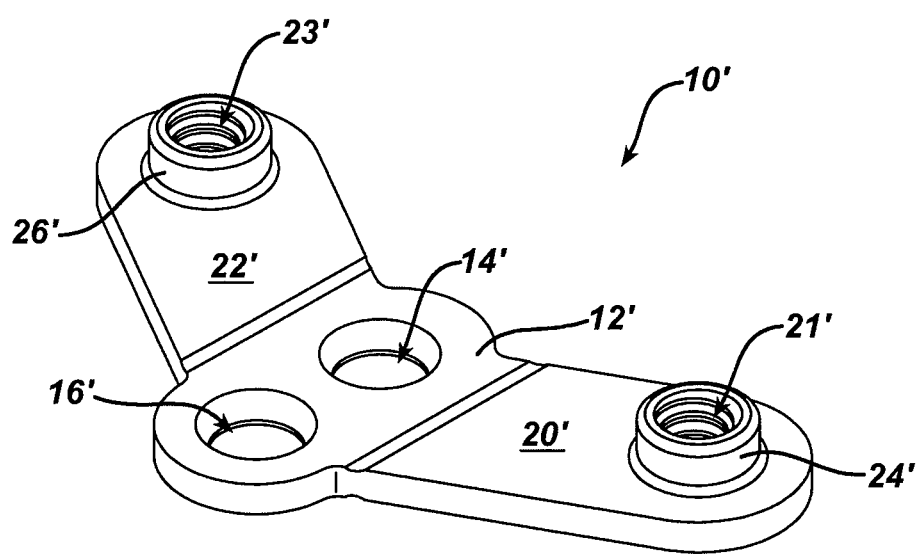
FIG. 2 is a top perspective view of a spinal fixation plate in accordance with yet another embodiment of the present invention.

FIGS. 1A-1B illustrate one embodiment of a spinal fixation plate 10 in accordance with the present invention. As shown, the plate 10 has a generally elongate central portion 12 that defines a longitudinal axis $L_c$ extending between proximal and distal ends 12a, 12b thereof. The shape of the central portion 12 can vary, but in an exemplary embodiment the proximal and distal ends 12a, 12b have a rounded or convex profile to avoid the risk of damage during implantation. The length $l_c$ of the central portion 12 can also vary, and the length $l_c$ will depend on the number of thru-bores formed therein. As shown in FIGS. 1A-1B, the central portion 12 includes three thru-bores 14, 16, 18 formed therein, and in particular it includes a first proximal thru-bore 14, a second central or middle thru-bore 16, and a third distal thru-bore 18. The thru-bores 14, 16, 18 are preferably aligned with one another along the longitudinal axis $L_c$ of the central portion 12, and each thru-bore 14, 16, 18 is preferably spaced equidistant apart from one another. A person skilled in the art will appreciate that the plate 10 can include any number of thru-bores formed therein. By way of non-limiting example, FIG. 2 illustrates a spinal fixation plate 10' that is substantially similar to plate 10, but that includes only a proximal thru-bore 14' and a distal thru-bore 16' formed therein.

The thru-bores 14, 16, 18 formed in the central portion 12 of the spinal fixation plate 10 can vary in shape and size, but they are preferably adapted to receive a fastening element, such as a spinal screw, therethrough for securing the plate 10 to bone. In the illustrated embodiments, shown in FIGS. 1A-2, each thru-bore 14, 16, 18, 14', 16' in the central portion 12, 12' has a substantially circular shape.

Still referring to FIGS. 1A-1B, the spinal fixation plate 10 also includes first and second branch portions 20, 22 that extend from opposed sides of the central portion 12. Each branch portion 20, 22 preferably has a generally elongate shape and includes a single thru-bore 21, 23 formed adjacent to a terminal end 20b, 22b thereof. The branch portions 20, 22 are preferably positioned just distal to the proximal end 12a of the central portion 12, such that the central portion 12 includes a proximal end 12a that extends proximally beyond the location at which the branch portions 20, 22 are attached to the central portion 12. The branch portions 20, 22 also preferably extend at an angle relative to the longitudinal axis $L_c$ of the central portion 12. In particular, each branch portion 20, 22 extends along a central axis $L_1$, $L_2$ that is disposed at an angle $\alpha_1$, $\alpha_2$ (FIG. 1B) relative to the longitudinal axis $L_c$ of the central portion 12, as measured toward the proximal end 12a of the central portion 12. The angle $\alpha_1$, $\alpha_2$ is preferably an acute angle, e.g., less than 90°, and in an exemplary embodiment, the angle $\alpha_1$, $\alpha_2$ is in the range of about 20° to 70°. As a result of the position of the branch portions 20, 22 relative to the central portion 12, the central axis $L_1$, $L_2$ of each branch portion 20, 22 meets at intersection point I that is positioned distal to a midpoint $14_m$ of the proximal thru-bore 14 in the central portion 12, and proximal to a midpoint $16_m$ of the middle thru-bore 16. More preferably, the intersection point I is positioned distal to the entire proximal thru-bore 14 formed in the central portion 12, and proximal to the entire middle thru-bore 16 such that the intersection point I resides at a location that is on the central portion 12 between the proximal and middle thru-bores 14, 16. The location of the intersection point I relative to the longitudinal axis $L_c$ of the central portion 12 can also vary depending on the angle $\alpha_1$, $\alpha_2$ of each branch portion 20, 22. For example, where the angle $\alpha_1$, $\alpha_2$ of each branch portion 20, 22 is the same, the intersection point I will be positioned along the longitudinal axis $L_c$. Alternatively, where the each angle $\alpha_1$, $\alpha_2$ of each branch portion 20, 22 differs, the intersection point I will be positioned at a location that is offset from the longitudinal axis $L_c$.

In use, the configuration of the branch portions 20, 22 allows the spinal fixation plate 10 to be implanted in various positions in the occiput in place of both of the prior art Y-shaped and T-shaped plates. As will be discussed in more detail below, the branch portions 20, 22 are configured to mate to one or more anchoring assemblies that are effective to mate a spinal fixation element, such as a spinal rod, to the plate 10. The branch portions 20, 22 can also optionally include one or more thru-bore formed therein for receiving a fixation element, such as a spinal screw to further facilitate fixation of the plate 10 to bone.

The shape of the thru-bore 21, 23 formed in each branch portion 20, 22 can also vary depending on the intended use. By way of non-limiting example, each thru-bore 21, 23 can have an oblong or ovular shape, as shown in FIGS. 1A-1B, or they can have a circular shape, as shown in FIG. 2. An oblong or ovular shape is advantageous in that it allows an anchoring assembly to be mated to the plate 10 and adjusted as desired relative to the branch portion 20, 22. In another embodiment, as shown in FIG. 2, each thru-bore 21', 23' can include a barrel or cylinder 24', 26' extending therefrom and/or therethrough and having threads formed therein. The cylinder 24', 26' allows an anchoring assembly to be attached to the spinal fixation plate 10', and more particularly the cylinder 24', 26' can be positioned through a bore formed in an anchoring assembly. This allows the anchoring assembly to be rotatably positioned relative to the plate until affixed in a desired position.

Anchoring assemblies are well known in the art, and they are typically used to attach a spinal fixation element, such as a spinal rod, to a spinal fixation plate. By way of non-limiting example, U.S. Pat. No. 6,524,315 of Selvitelli et al. entitled "Orthopaedic Rod/Plate Locking Mechanism," and U.S. Pat. No. 6,547,790 of Harkey, III et al. entitled "Orthopaedic Rod/Plate Locking Mechanism and Surgical Methods" each describe anchoring assemblies that can be used to mate a spinal fixation rod to a spinal plate. In general, each anchoring assembly includes a rod-receiving feature and a fastening element that is adapted to extend through a thru-bore formed in a spinal fixation plate to mate the anchoring assembly to the spinal fixation plate. A person skilled in the art will appreciate that a variety of anchoring assemblies and other techniques can be used with the present invention to mate a spinal fixation element, such as a spinal rod, to the spinal plate 10. Moreover, the anchoring assembly can be fixedly attached to or integrally formed with the spinal fixation plate 10.

Referring back to FIGS. 1A-1B, the spinal fixation plate 10 of the present invention can also include at least one bend zone 28, 30 formed therein for allowing the branch portions 20, 22 to be bend forward and backward relative to a front surface 10a and/or a back surface 10b (FIG. 1A) of the central portion 12. In particular, the bend zones 28, 30 preferably allow the branch portions 20, 22 to extend in a plane that intersects or is transverse to the horizontal plane in which the central portion 12 extends. A variety of techniques can be used to allow bendable movement of each branch portion 20, 22, but in an exemplary embodiment the bend zones 28, 30 are formed at the intersection between each branch portion 20, 22 and the central portion 12, and they are formed from grooves or channels 28a, 30a that extend across at least one of the front surface 10a or the back surface 10b of the spinal fixation plate 10. In an exemplary embodiment, to facilitate bendable movement in both a forward and backward direction, the spinal fixation plate 10 includes a first channel 28a, 30a formed in the top surface 10a of the plate 10 between each branch portion 20, 22 and the central portion 12, and a second, opposed channel 28b, 30b (only a portion of which is shown) formed in the bottom surface 10b of the plate 10, as shown in FIG. 1A. A person skilled in the art will appreciate that a variety of other techniques can be used to provide bendable movement of one or more portions of the spinal fixation plate 10, and that the bend zones can be formed anywhere on the plate 10.

The present invention also provides several extension members that can be used to provide additional thru-bores to the spinal fixation plate 10. The extension members are particularly advantageous in that they allow a surgeon to modify an existing plate, rather than requiring a large inventory of plates having particular configurations. A person skilled in the art will appreciate that the extension members can have a variety of configurations, and that they can be adapted to couple to the central portion 12 of the fixation plate 10, and/or to the branch portions 20, 22 for providing additional midline and/or lateral thru-bores. The extension members can also be used in conjunction with one or more anchoring assemblies.

Figure 3:
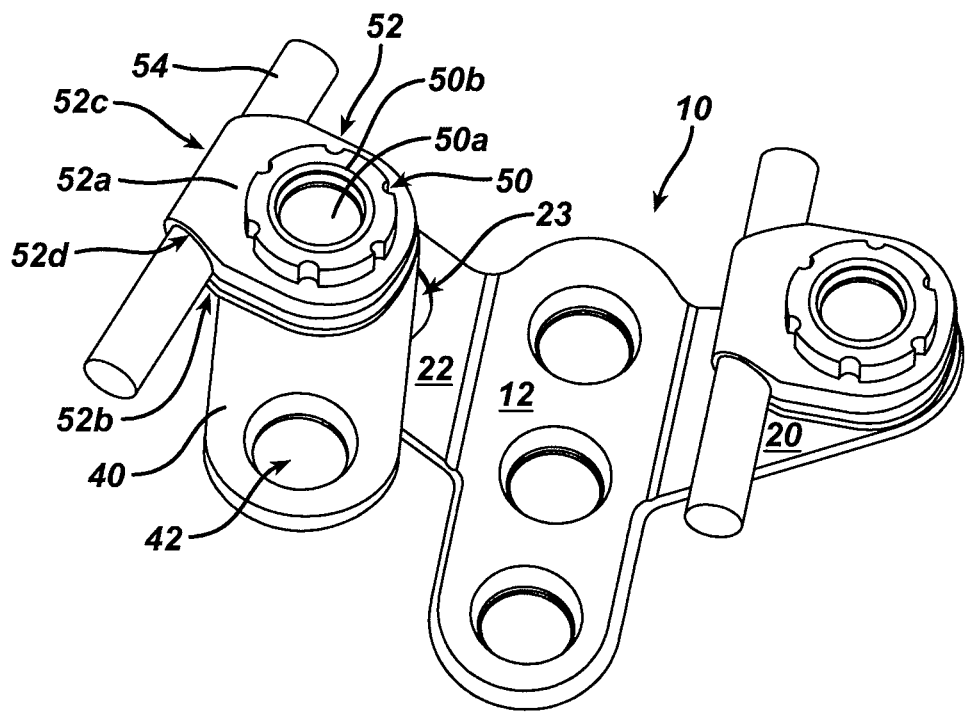
FIG. 3 is a top perspective view of the spinal fixation plate shown in FIG. 1A having an extension member and a clamp member containing a spinal fixation rod mated thereto.

Referring to FIG. 3, the spinal fixation plate 10 can also be used with a variety of devices that are effective to mate a spinal fixation element, such as spinal rod, to the plate 10. In particular, FIG. 3 illustrates a clamp 52 that is mated to thru-hole 23 in the second branch portion 22 of the plate 10 by fastening element 50 that includes two components which work together to lock the clamp 52 to the plate 10. The clamp 52 generally includes top and bottom portions 52a, 52b that are mated to one another by a hinged portion 52c. The hinged portion 52c defines a pathway 52d extending therethrough for receiving a spinal fixation element 54, and it allows the top and bottom portions 52a, 52b to be moved relative to one another. In use, one component of the fastening element 50 is disposed through a thru-hole (hidden) formed in each of the top and bottom portions 52a, 52b of the clamp 52, and through the desired thru-hole in the spinal fixation plate 52. As shown in FIG. 3, a portion of the fastening element 50 extends through the clamp 52, through an extension member 40, which will be discussed in detail below, and through a thru-bore 23 formed in the spinal fixation plate 20. When the components of the fastening element 50 are locked together, they will bring the top and bottom portions 52a, 52b of the clamp 52 toward one another to engage the spinal fixation element 54 within the pathway 52d in the hinged portion 52c, thereby mating the fixation element 54 to the plate. A person skilled in the art will appreciate that a variety of fastening elements can be used to mate the clamp 52 to the plate 10. In the illustrated embodiment, the fastening element 50 includes a threaded member, e.g., a screw 50a, and a locking nut 50b for mating with the threaded member 50a.

Figure 4:
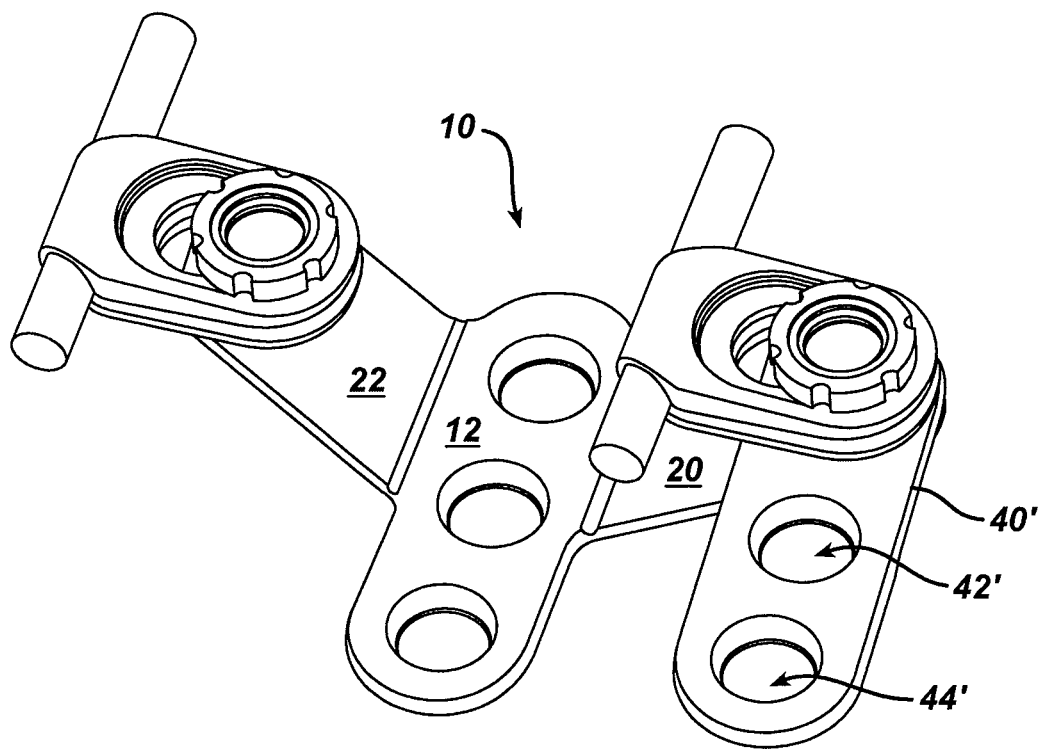
FIG. 4 is a top perspective view of the spinal fixation plate shown in FIG. 1A having another embodiment of an extension member and having a clamp member containing a spinal fixation rod mated thereto.

As indicated above, FIG. 3 also illustrates one embodiment of an extension member 40 that is coupled to the spinal fixation plate 10 of FIGS. 1A-1B. As shown, the extension member 40 has a generally elongate shape that is similar to the shape of the central portion 12 of the spinal fixation plate 10. A first thru-bore (hidden) is formed in the extension member 40 and it is adapted to be juxtapositioned on one of the thru-bores formed in a portion of the spinal fixation plate 10. By way of non-limiting example, FIG. 3 illustrates the first thru-bore juxtapositioned on thru-bore 23 formed in the second branch portion 22 of the plate 10. The extension member 40 is mated to the thru-bore 23 formed in the second branch portion 22 by the fastening element 50 which extends through the first thru-bore (hidden) in the extension member 40 and the thru-bore 23 formed in the second branch portion 22. The extension member 40 can also include one or more additional thru-bores formed therein for receiving a fastening element, such as a spinal screw. As shown in FIG. 3, the extension member 40 includes a second thru-bore 42 formed therein and positioned a distance apart from the first thru-bore (hidden). FIG. 4 illustrates another embodiment of an extension member 40' having first, second, and third thru-bores 42', 44' (the first thru-bore is hidden) formed therein.

Figure 5A:
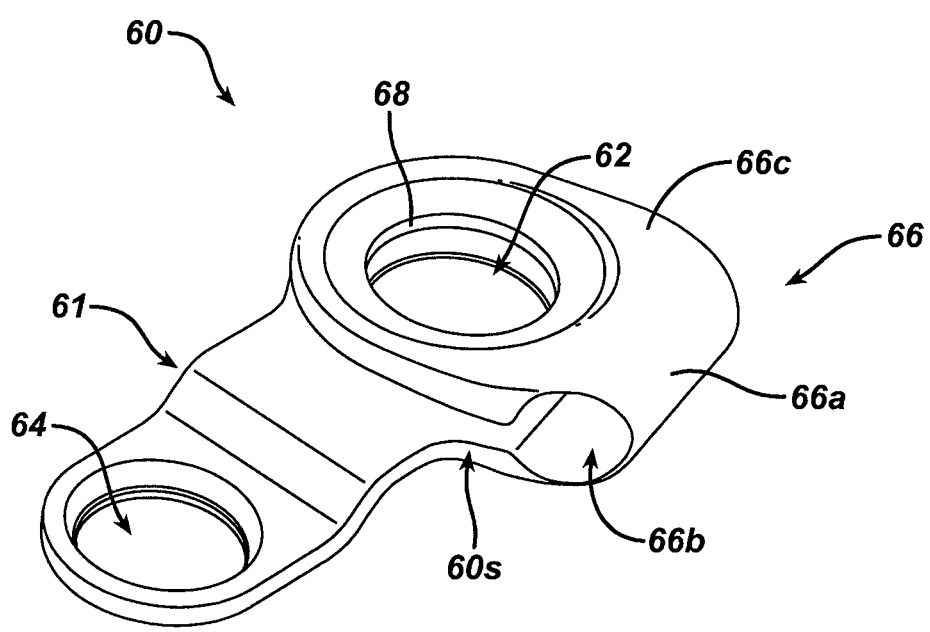
FIG. 5A is a top perspective view of yet another embodiment of an extension member having a clamp member formed integrally therewith.
Figure 5B:
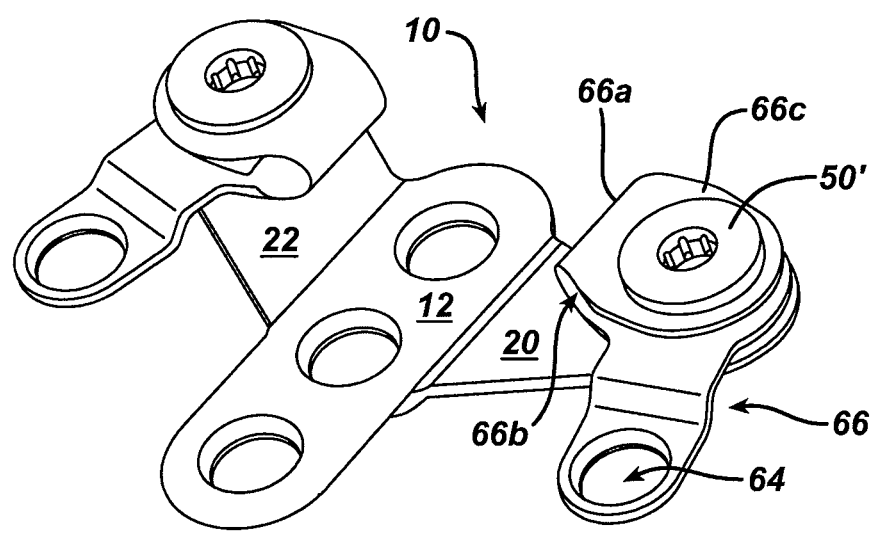
FIG. 5B is a top perspective view of the extension member shown in FIG. 5A mated to the spinal fixation plate shown in FIG. 1A by a fastening element.

FIGS. 5A-5B illustrate yet another embodiment of an extension member 60 in accordance with the present invention. As shown, the extension member 60 is somewhat similar to extension members 40 and 40' shown in FIGS. 3 and 4, however it includes a clamp mechanism formed integrally therewith. In general, the extension member 60 has a substantially elongate shape, and it includes first and second thru-bores 62, 64 formed therein and positioned a distance apart from one another. The first thru-bore 62 is preferably adapted to be juxtapositioned on a thru-bore formed in the spinal fixation plate 10, and the second thru-bore 64 is preferably positioned in a plane that is substantially parallel to a plane in which the first thru-bore 62 lies. This can be achieved by providing one or more bends 61 in the extension member 60. The bend 61 is preferably configured such that the second thru-bore 64 resides in the same plane as a thru-bore formed in the spinal fixation plate 10 when the extension member 60 is mated to the plate 10, thus allowing the second thru-bore 64 to be positioned against bone to which the plate 10 is attached. In other embodiments (not shown), the second thru-bore 64 can be positioned in a plane that is at an angle to the plane containing the first thru-bore 62. The thru-bore 64 can also be angularly oriented relative to the first thru-bore 62. A person skilled in the art will appreciate that the extension member 60 can have a variety of configurations, and it can include any number of addition thru-bores formed therein.

The extension member 60 also includes a clamp mechanism 66 that is coupled to a sidewall $60_s$ of the extension member 60 adjacent to the first thru-bore 62. The clamp mechanism 66 includes a hinged portion 66a defining a pathway 66b extending therethrough for receiving a spinal fixation element, and a top portion 66c having a thru-bore 68 formed therein that is juxtapositioned on the first thru-bore 62 in the extension member 60. In use, as shown in FIG. 5B, a fastening element 50' can be inserted through the thru-bore 68 in the top portion 66c of the clamp mechanism 66, and through the first thru-bore 62 formed in the extension member 60 to secure the top portion 66c to the extension member 60, thereby closing the hinged portion 66a to engage a spinal fixation element disposed through the pathway 66b formed therein. The fastening element 50' can also extend through one of the thru-bores in the spinal fixation plate 10, e.g., thru-bore 21 formed in the first branch portion 20, to mate the extension member 60 to the plate 10, and thereby mate a spinal fixation element, such as a spinal rod, to the plate 10.

Figure 6:
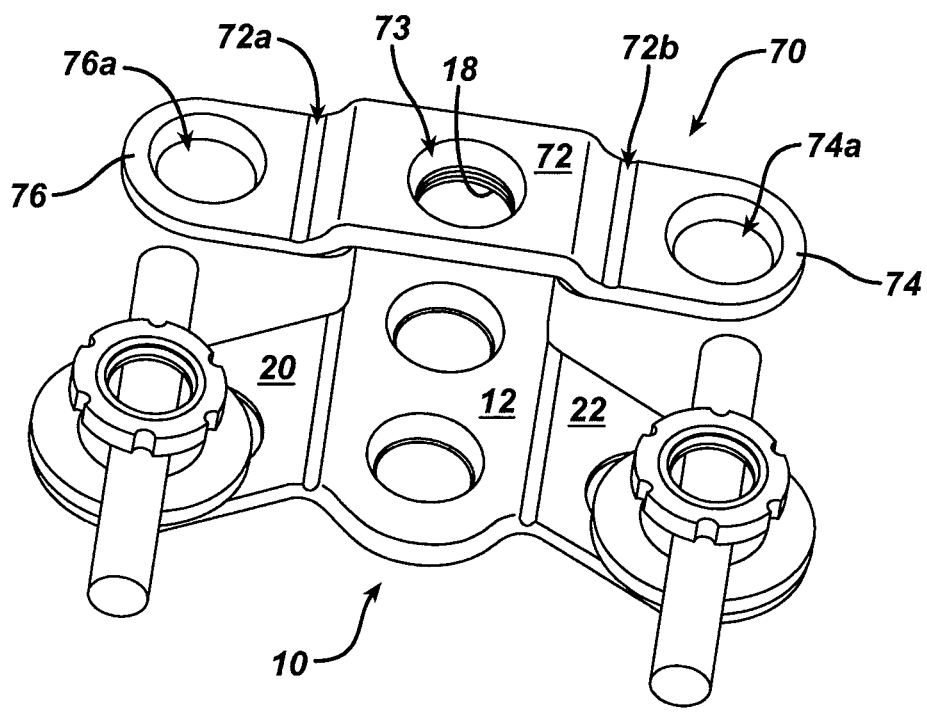
FIG. 6 is a perspective view of yet another embodiment of an extension member mated to a mid-line thru-bore formed in the spinal fixation plate shown in FIG. 1A.

FIG. 6 illustrates yet another embodiment of an extension member 70 in accordance with the present invention. In this embodiment, the extension member 70 is particularly designed for mating with the central portion 12 of the spinal fixation plate 10. As shown, the extension member 70 has a generally elongate configuration with a central portion 72 having a middle thru-bore 73 formed therein, and opposed terminal portions 74, 76, each having a thru-bore 74a, 76a formed therein and positioned on opposed sides of the middle thru-bore 73. The central portion 72 is adapted to be juxtapositioned on one of the thru-bores formed in the central portion 12 of the plate 10, e.g., on thru-bore 18, and the extension member 70 can be mated to the plate 10 by inserting a fastening element through both thru-bores 73, 18. As a result, the thru-bores 74a, 76a formed in the terminal portions 74, 76 are positioned on opposed sides of the central portion 12 of plate 10 for receiving a fastening element, such as a spinal screw.

In a further embodiment, the terminal portions 74, 76 of the extension member 70 can reside in a plane that is substantially parallel to a plane of the central portion 72 such that when the extension member 70 is mated to a spinal fixation plate 10, as shown, the thru-bores 74a, 76a formed in the terminal portions 74, 76 lie in the same plane as the thru-bore 18 formed in the central portion 12 of the plate 10. This allows the terminal portions 74, 76 to be positioned against the bone to which the plate 10 is attached. This can be achieved by forming one or more bends 72a, 72b in the extension member 70 between the central portion 72 and the terminal portions 74, 76. The bends 72a, 72b can also be adapted to allow bendable movement of the terminal portions 74, 76 to allow them to be positioned at an angle relative to the central portion 72 as desired.

Figure 7A:
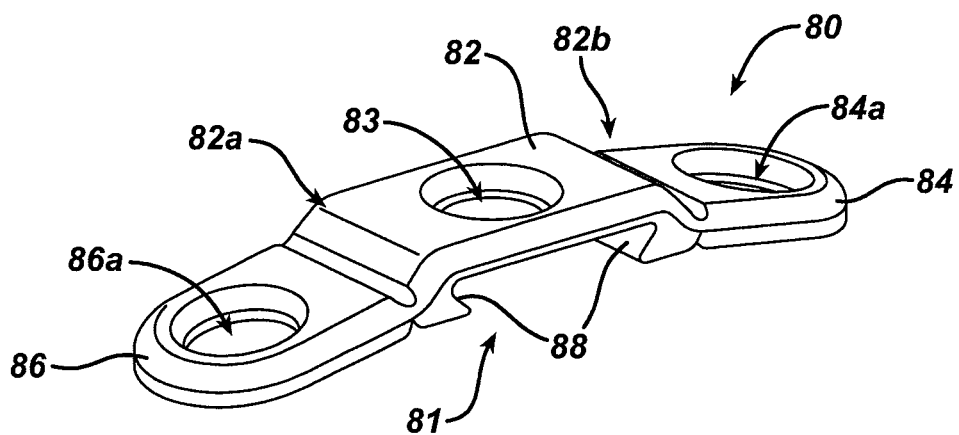
FIG. 7A is a perspective view of anther embodiment of an extension member having a dovetail configuration for mating with a spinal fixation plate.
Figure 7B:
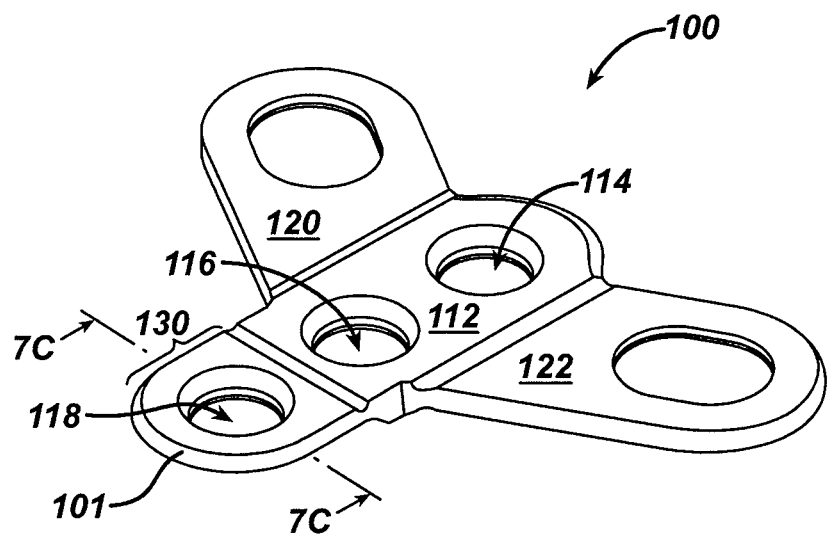
FIG. 7B is a perspective view of the spinal fixation plate for use with the extension member shown in FIG. 7A.

FIG. 7A illustrates another embodiment of an extension member 80 for use with a spinal fixation plate 100 shown in FIG. 7B. A person skilled in the art will appreciate that, while the extension member 80 is described in connection with plate 100, that the fixation plate can have virtually any configuration, and a variety of known spinal fixation plates can be adapted for use with the extension member 80. As shown in FIG. 7A, the extension member 80 is substantially similar to extension member 70 shown in FIG. 6, and it includes a central portion 82 having a middle thru-bore 83 formed therein, and opposed terminal portions 84, 86, each having a thru-bore 84a, 86a formed therein and positioned on opposed sides of the middle thru-bore 83. One significant difference, however, is that extension 80 includes a lower surface 81 that has a mating feature formed thereon for mating with a complementary mating feature on the spinal fixation plate 100.

Figure 7C:
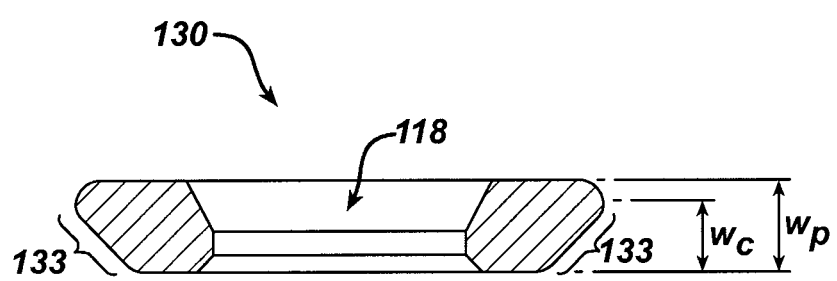
FIG. 7C is a cross-sectional view of a portion of the plate shown in FIG. 7B taken across line 7C-7C.

While a variety of complementary mating features can be used to mate the extension member 80 to the plate 100, in the illustrated embodiment, the complementary mating feature is a dovetail connection having complementary components 88, 133. In particular, the lower surface 81 of the extension member 80 includes a female dovetail 88, and the plate 100 includes a complementary, male dovetail 133. The male dovetail 133 on the plate 100 can be in the form of a chamfer, shown in FIG. 7C, that extends around a perimeter 101 of a distal portion 130 of the plate 100 on a lower surface thereof. While the size of the chamfer 133 can vary depending on the size of the complementary female dovetail 88 on the extension member 80, in an exemplary embodiment the chamfer 133 has a width $w_c$ that is equal to or more preferably greater than about half of the width $w_p$ of the distal portion 130 of the plate 100, as shown in FIG. 7C.

In use, the male and female dovetail components 88, 133 are adapted to slidably mate to one another, such that the extension member 80 can be slid onto the distal portion 103 of the central portion 112 of the fixation plate 100, and the middle thru-bore 83 in the extension plate 80 can be aligned with one of the distal thru-bore 118 in the plate 100. The dovetail components 88, 103 can also optionally be dimensioned to provide a frictional or interference fit to fixedly or securely mate the extension member 80 to the fixation plate 100. One of ordinary skill in the art will appreciate that the male and female dovetail members 88, 103 can be reversed, or that the complementary mating feature can have any other form, such as a T-slot. Moreover, the extension member 80 can have a variety of other configurations, and it can be adapted to attach to any portion of a spinal fixation plate.

One of ordinary skill in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A spinal fixation kit for fixation of an occiput to a spinal column, comprising:
   an occipital plate having an elongate central portion with at least two thru-bores formed therein and positioned along a central longitudinal axis thereof, and first and second branch portions that extend from opposed sides of the elongate central portion; and
   an extension plate having a mating channel for removably mating to the elongate central portion, the extension plate having a length along a longitudinal axis thereof that is greater than a width of the extension plate and having a plurality of thru-bores formed therein,
   wherein, when the elongate central portion is received within the mating channel of the extension plate, the longitudinal axis of the extension plate is transverse to the central longitudinal axis of the occipital plate, and at least one of the plurality of thru-bores in the extension plate is aligned with at least one of the thru-bores formed in the occipital plate.

2. The spinal fixation kit of claim 1, wherein the extension plate is configured to frictionally engage the occipital plate.

3. The spinal fixation kit of claim 1, wherein the extension plate is slidably matable to the occipital plate along the central longitudinal axis of the occipital plate, and wherein the extension plate is prevented from movement in a direction transverse to the central longitudinal axis of the occipital plate.

4. The spinal fixation kit of claim 1, wherein the mating channel of the extension plate includes a mating element formed thereon for slidably mating with a complementary mating element formed on the occipital plate.

5. The spinal fixation kit of claim 4, wherein the complementary mating elements comprise dovetail components.

6. The spinal fixation kit of claim 1, wherein each branch portion includes at least one thru-bore formed therein.

7. The spinal fixation kit of claim 1, wherein the first branch portion extends along a first central axis, and the second branch portion extends along a second central axis that intersects the first central axis.

8. The spinal fixation kit of claim 1, wherein the plurality of thru-bores in the elongate central portion of the occipital plate comprises a proximal-most thru-bore, a distal-most thru-bore, and a central thru-bore, and wherein one of the plurality of thru-bores in the extension plate is juxtapositioned on the distal-most thru-bore formed in the elongate central portion of the occipital plate when the elongate central portion is received within the mating channel of the extension plate.

9. A spinal fixation kit for fixation of an occiput to a spinal column, comprising:
   a spinal fixation plate comprising an occipital plate having
      an elongate central portion with a plurality of thru-bores formed therein and aligned along a longitudinal axis of the elongate central portion, and
      first and second branch portions extending from the elongate central portion in a direction transverse to the longitudinal axis of the elongate central portion, wherein the elongate central portion and the first and second branch portions are monolithic; and
   an extension plate having a plurality of thru-bores formed therein, the plurality of thru-bores all being aligned along a longitudinal axis of the extension plate, a mid portion of the extension plate being configured to slide along the longitudinal axis of the elongate central portion with opposed terminal portions of the extension plate extending beyond opposed longitudinal sides of the elongate central portion to frictionally engage the elongate central portion of the spinal fixation plate to juxtaposition one of the plurality of thru-bores in the extension plate on one of the plurality of thru-bores in the elongate central portion of the spinal fixation plate.

10. The spinal fixation kit of claim 9, wherein, when the extension plate is mated to the elongate central portion, the extension plate is prevented from moving in a direction transverse to the longitudinal axis of the elongate central portion.

11. The spinal fixation kit of claim 9, wherein the extension plate includes a mating element configured to engage opposed longitudinal sides of the elongate central portion.

12. The spinal fixation kit of claim 11, wherein the mating element-comprises a dovetail component.

13. The spinal fixation kit of claim 9, wherein the mid portion has a central thru-bore formed therein, and each of the opposed terminal portions have a thru-bore formed therein.

14. The spinal fixation kit of claim 13, wherein the extension plate is configured to engage the elongate central portion such that the central thru-bore in the extension plate is juxtapositioned on one of the plurality of thru-bores in the elongate central portion of the spinal fixation plate.

15. The spinal fixation kit of claim 9, wherein the first and second branch portions each include at least one thru-bore formed therein.

16. The spinal fixation kit of claim 1, wherein the first and second branch portions and the elongate central portion are formed from a unitary member.

17. The spinal fixation kit of claim 1, further comprising a clamping mechanism coupled to the first branch portion or the second branch portion of the extension plate.

18. The spinal fixation kit of claim 17, wherein the clamping mechanism includes a hinged portion configured to engage a spinal fixation element slidably disposed therethrough.

19. The spinal fixation kit of claim 11, wherein the elongate central portion has a complementary mating element that extends along the opposed longitudinal sides of the elongate central portion.

* * * * *